(12) United States Patent
Reis et al.

(10) Patent No.: US 10,278,851 B2
(45) Date of Patent: May 7, 2019

(54) SYSTEMS AND METHODS FOR DELIVERING STENT GRAFTS

(71) Applicant: PQ Bypass, Inc., Sunnyvale, CA (US)

(72) Inventors: Gene Reis, San Jose, CA (US); Kumar Jambunathan, Sunnyvale, CA (US); Steven Tyler, San Mateo, CA (US)

(73) Assignee: PQ Bypass, Inc., Sunnyvale, CA (US)

( * ) Notice: Subject to any disclaimer, the term of this patent is extended or adjusted under 35 U.S.C. 154(b) by 0 days.

(21) Appl. No.: 15/723,933

(22) Filed: Oct. 3, 2017

(65) Prior Publication Data
US 2018/0098869 A1 Apr. 12, 2018

Related U.S. Application Data

(60) Provisional application No. 62/405,479, filed on Oct. 7, 2016.

(51) Int. Cl.
| | | |
|---|---|---|
| *A61F 2/95* | (2013.01) | |
| *A61F 2/958* | (2013.01) | |
| *A61F 2/954* | (2013.01) | |
| *A61F 2/962* | (2013.01) | |
| *A61F 2/07* | (2013.01) | |

(52) U.S. Cl.
CPC ............ *A61F 2/958* (2013.01); *A61F 2/954* (2013.01); *A61F 2/962* (2013.01); *A61F 2/07* (2013.01); *A61F 2002/9517* (2013.01)

(58) Field of Classification Search
CPC .. A61F 2/07; A61F 2/954; A61F 2/958; A61F 2/962; A61F 2002/9517; A61F 2002/9665; A61F 2/966
See application file for complete search history.

(56) References Cited

U.S. PATENT DOCUMENTS

| | | |
|---|---|---|
| 5,078,735 A | 1/1992 | Mobin-Uddin |
| 5,211,683 A | 5/1993 | Maginot |
| (Continued) | | |

FOREIGN PATENT DOCUMENTS

| | | |
|---|---|---|
| WO | WO-2007127802 A2 | 11/2007 |
| WO | WO-2018067537 A1 | 4/2018 |

OTHER PUBLICATIONS

International Search Report dated Nov. 27, 2017 for International PCT Patent Application No. PCT/US2017/054900.

*Primary Examiner* — Ryan J. Severson
*Assistant Examiner* — Christian D Knauss
(74) *Attorney, Agent, or Firm* — Wilson Sonsini Goodrich and Rosati, P.C.

(57) ABSTRACT

A delivery catheter comprises an inner shaft and an outer sheath. A stent-graft is held on a region of the inner shaft. An enlarged diameter distal region of the outer sheath constrains the stent-graft. Its retraction allows the stent-graft to deploy. A finger wheel on a handle is used to retract the outer sheath and is coupled to a sliding block with cable(s). The sliding block is coupled to the outer sheath and is held within a sliding track. The wheel can be actuated to tension the cable(s) and deform latch(es) coupled to sliding block, freeing them from slot(s) in the sliding track and allowing retraction of the sliding block and the outer sheath. A reinforcement sleeve is coupled to a smaller diameter proximal region of the outer sheath. A gap between the outer sheath distal region and the reinforcement sleeve allows the distal outer shaft region to be retracted.

45 Claims, 10 Drawing Sheets

(56) References Cited

U.S. PATENT DOCUMENTS

| | | | |
|---|---|---|---|
| 5,693,088 A * | 12/1997 | Lazarus | A61F 2/07 606/195 |
| 5,830,222 A | 11/1998 | Makower | |
| 6,068,638 A | 5/2000 | Makower | |
| 6,190,353 B1 | 2/2001 | Makower et al. | |
| 6,231,587 B1 | 5/2001 | Makower | |
| 6,379,319 B1 | 4/2002 | Garibotto et al. | |
| 6,464,665 B1 | 10/2002 | Heuser | |
| 6,475,226 B1 | 11/2002 | Belef et al. | |
| 6,508,824 B1 | 1/2003 | Flaherty et al. | |
| 6,544,230 B1 | 4/2003 | Flaherty et al. | |
| 6,579,311 B1 | 6/2003 | Makower | |
| 6,585,650 B1 | 7/2003 | Solem | |
| 6,655,386 B1 | 12/2003 | Makower et al. | |
| 6,694,983 B2 | 2/2004 | Hall et al. | |
| 6,719,725 B2 | 4/2004 | Milo et al. | |
| 6,858,038 B2 | 2/2005 | Heuser | |
| 6,976,990 B2 | 12/2005 | Mowry | |
| 7,004,173 B2 | 2/2006 | Sparks et al. | |
| 7,083,631 B2 | 8/2006 | Houser et al. | |
| 7,134,438 B2 | 11/2006 | Makower et al. | |
| 7,300,459 B2 | 11/2007 | Heuser | |
| 7,316,655 B2 | 1/2008 | Garibotto et al. | |
| 7,374,567 B2 | 5/2008 | Heuser | |
| 7,402,141 B2 | 7/2008 | Heuser | |
| 7,553,323 B1 * | 6/2009 | Perez | A61F 2/962 623/1.11 |
| 7,729,738 B2 | 6/2010 | Flaherty et al. | |
| 8,062,321 B2 | 11/2011 | Heuser et al. | |
| 9,259,340 B2 | 2/2016 | Heuser et al. | |
| 9,301,830 B2 | 4/2016 | Heuser et al. | |
| 2005/0273151 A1 | 12/2005 | Fulkerson et al. | |
| 2006/0259123 A1 * | 11/2006 | Dorn | A61F 2/91 623/1.12 |
| 2006/0282152 A1 * | 12/2006 | Beyerlein | A61F 2/95 623/1.11 |
| 2007/0055340 A1 * | 3/2007 | Pryor | A61F 2/95 623/1.11 |
| 2007/0168014 A1 | 7/2007 | Jimenez et al. | |
| 2009/0036967 A1 * | 2/2009 | Cummings | A61F 2/95 623/1.11 |
| 2010/0036472 A1 | 2/2010 | Papp | |
| 2010/0036475 A1 | 2/2010 | Castaneda | |
| 2010/0076541 A1 | 3/2010 | Kumoyama | |
| 2012/0239137 A1 | 9/2012 | Heuser et al. | |
| 2014/0236279 A1 | 8/2014 | Dillon et al. | |
| 2016/0074188 A1 | 3/2016 | Ryan et al. | |
| 2016/0074189 A1 * | 3/2016 | Cummins | A61F 2/966 623/1.11 |
| 2016/0175087 A1 | 6/2016 | Heuser et al. | |

* cited by examiner

SYSTEMS AND METHODS FOR DELIVERING STENT GRAFTS

CROSS-REFERENCE

This application claims the benefit of U.S. Provisional Application No. 62/405,479, filed Oct. 7, 2016, which application is incorporated herein by reference.

BACKGROUND

1. Field of the Invention

The present disclosure relates generally to medical methods and devices. More particularly, the present disclosure relates to methods and devices for the endovascular placement of a stent-graft, such as from an artery, through an adjacent vein, and back to the artery in order to bypass an occlusion in the artery, typically a femoral artery.

Peripheral arterial occlusive disease results from atherosclerotic processes which cause a blockage or stenosis within a peripheral artery, typically a femoral artery, most commonly the superficial femoral artery. As the disease progresses, resistance to blood flow down the patient's leg reduces distal perfusion of the leg. In the most severe cases, the disease can lead to limb ischemia which can have serious complications, including gangrene and loss of the leg.

Peripheral arterial occlusive disease in the femoral artery can be treated in many of the same ways as arterial disease elsewhere in the body. Endarterectomy and atherectomy can both be used to remove the occlusive deposits and restore blood flow. Bypass grafts may also be placed from a location proximal to the occlusion to a location distal to the occlusion in order to provide an unobstructed path for blood to flow in the artery. Such bypass grafts are most commonly placed in open vascular surgeries where the bypass grafts may be attached to the femoral or other artery by conventional anastomotic connections. More recently, it has been proposed to perform such procedures endovascularly to place a bypass stent-graft from the artery, through an adjacent vein, and back to the artery in order to bypass the occlusion.

Of particular interest to the present disclosure, Dr. James Joye has performed such endovascular stent-graft bypass procedures using commercially available catheters and tools.

While such protocols are very effective in the hands of a highly skilled vascular surgeon, they are lengthy, can be difficult to perform, and many surgeons would not feel confident trying to perform these procedures using conventionally available catheters and tools. For these reasons, it would be desirable to provide improved protocols and specialized catheters and surgical tools which reduce the technical difficulty of performing such endovascular stent-graft femoral bypass procedures. At least some of these objectives will be met by the systems, devices, and methods described herein below.

2. Description of the Background Art

Systems and methods for placing stent-grafts for bypassing peripheral and other occlusions are described in U.S. Pat. Nos. 5,078,735 and 5,211,683. A particular method for performing an external femoropopliteal bypass graft is described in WO2007/127802 and US 2010/0036475. U.S. Pat. Nos. 6,464,665 and 7,374,567, both describe catheters useful for capturing a needle and placing a stent across adjacent vessels. Other relevant patents include U.S. Pat. Nos. 5,830,222; 6,068,638; 6,190,353; 6,231,587; 6,379,319; 6,475,226; 6,464,665; 6,508,824; 6,544,230; 6,655,386; 6,579,311; 6,585,650; 6,694,983; 6,719,725; 6,858,038; 6,976,990; 7,004,173; 7,083,631; 7,134,438; 7,300,459; 7,316,655; 7,374,567; 7,402,141; 7,729,738; 8,062,321; 9,259,340; and 9,301,830.

SUMMARY

The present disclosure provides systems, devices, and methods for delivering medical implants, such as stent grafts and bypass grafts, to bodily vessels, such as blood vessels like peripheral arteries. The peripheral artery will most commonly be a femoral artery, such as a superficial femoral artery or a common femoral artery, but could also be an iliac artery, a popliteal artery, a posterior tibial artery, a peroneal artery, an anterior tibial artery, and the like. For consistency, references below will typically be made to the femoral artery. The methods may comprise a series of steps which are performed endovascularly in a femoral artery, typically the superficial femoral artery including the popliteal artery which is an extension of the superficial femoral artery, as well as in one or more adjacent femoral veins including a popliteal vein which is an extension of the femoral vein. The methods may comprise forming a proximal penetration from the femoral artery to an adjacent femoral vein at a location above the occlusion. A penetration guidewire may be advanced down the femoral artery, through the proximal penetration, and into the femoral vein. Typically, the penetration guidewire will be advanced contralaterally over the iliac arch from the opposite leg of the patient.

After the penetration guidewire has been advanced into the femoral vein, the penetration guidewire will be pulled through an external penetration below the occlusion, typically in the popliteal vein. The penetration catheter may then be advanced over the penetration guidewire from the femoral artery into the femoral vein, and a penetration tool carried by the penetration catheter may be penetrated from the femoral vein into the femoral artery at a location below the occlusion to form a distal penetration. After both the proximal and distal penetrations are formed, a graft placement guidewire may be positioned from the femoral artery through the proximal penetration, down the femoral vein, and through the distal penetration back into the femoral artery. A stent-graft may then be deployed from a delivery catheter apparatus introduced over the stent-graft placement guidewire to complete the bypass of the occlusion. The delivery catheter apparatuses of the present disclosure may be delivered over guidewires and typically include a retractable outer sheath which may be proximally retracted to release a stent-graft from constraint, allowing the stent-graft to self-expand into the target location. The delivery catheter apparatuses may be provided with latch mechanisms and other structural features to facilitate outer sheath retraction, as well as with other structural features to prevent undesired compression or shortening with minimal loss of flexibility.

Placing the stent-graft placement guidewire typically comprises advancing the stent-graft placement guidewire (or an exchange wire) through a hollow lumen in the penetration tool after said tool has been advanced from the femoral vein into the femoral artery. Typically, a 0.014 in. or other small exchange wire is first deployed through penetration tool, and is then exchanged for a 0.035 in. or other larger stent-graft placement guidewire which is used to position a stent-graft delivery catheter to deliver the stent graft(s) as described more fully below. Use of the heavier guidewire may be advantageous since the stent-graft placement guidewire will not be controlled at its distal end.

Deploying the stent-graft over the stent-graft placement guidewire will typically comprise releasing the stent-graft from constraint so that the stent-graft then can self-expand. For example, the stent-graft may be composed of a Nitinol or other shape-memory material, typically covered by a graft material, and may be constrained in a tubular sheath of a stent-graft placement catheter which is advanced over the stent placement guidewire. The sheath may then be retracted to deploy the stent. Alternatively, in some instances, the stent graft may be balloon expandable or expandable for axial contraction, e.g., using a tether or other puller to draw the end of the scaffold together to cause radial expansion. In some cases, one stent will be sufficient to form the bypass graft. For longer occlusions, two or more stent grafts may be deployed in an overlapping fashion. In still other embodiments, it may be desirable to initially place covered or uncovered stents, either self-expanding or balloon expandable, in either or both of the anastomotic penetrations between the artery and vein before deploying the stent-graft.

As used herein and in the claims, the directions of "up," "upward," "down," and "downward" are intended to mean the directions relative to the patient's head and feet, where the head will generally be considered up or upward and the feet will be considered down or downward.

Aspects of the present disclosure provide catheter apparatuses for delivering one or more implants. An exemplary catheter apparatus may comprise an inner shaft and an outer sheath. The inner shaft may have a proximal portion, a distal portion, and an implant holding region at the distal portion. The outer sheath may be disposed at least over the implant holding region of the inner shaft. The outer sheath may be configured to be proximally retracted to expose an implant placed in the implant holding region to allow the implant to be deployed. The retractable outer sheath may have a proximal end and a distal end. The catheter apparatus may further comprise at least one retractable latch and at least one cable coupled thereto. The at least one retractable latch may be coupled to the proximal end of the outer sheath and may be configured to resist retraction of the outer sheath. The latch mechanism may be configured to be released upon tensioning of the at least one cable over a threshold force so that the proximal retraction of the at least one cable over the threshold force proximally retracts the at least one retractable latch and the outer sheath. The implant may comprise a stent-graft, such as a femoral-popliteal stent-graft, and the implant may be is self-expanding.

The catheter apparatus may further comprise a handle body enclosing the proximal portion of the inner shaft and the proximal end of the outer sheath. The handle body may comprise an inner track, and the at least one retractable latch may be configured to releasably couple to the inner track of the handle body to resist proximal retraction. The tensioning of the at least one cable over the threshold force may release the at least one retractable latch from the inner track of the handle body. The inner track of the handle body may comprise one or more slots, and the at least one retractable latch may be biased to push outwardly into the one or more slots to resist proximal retraction. The tensioning of the at least one cable over the threshold force may retract the at least one retractable latch from the one or more slots thereby allowing proximal retraction of the outer sheath. The one or more slots may comprise a plurality of slots.

Alternatively or in combination, the at least one retractable latch may be biased to push outwardly against the inner track of the handle body to provide friction to resist proximal retraction. The tensioning of the at least one cable over the threshold force may change a configuration of the at least one retractable latch to release from the inner track of the handle body.

The catheter apparatus may further comprise a sliding block coupling the proximal end of the outer sheath to the at least one retractable latch. The sliding block may be configured to slide along the inner track of the handle body.

The catheter apparatus may further comprise a pulley operatively coupled to the at least one cable. The pulley may be configured to be actuated to proximally retract the at least one cable. The spool may be housed within the handle body. The pulley may comprise a rotatable spool. The catheter apparatus may further comprise a finger wheel coupled to handle body and the rotatable spool, and the finger wheel may be configured to be spun to actuate the pulley.

The at least one latch may comprise a plurality of latches and the at least one cable may comprise a plurality of cables, each cable of the plurality being coupled to a corresponding latch of the plurality of latches.

The catheter apparatus may further comprise a distal nose coupled to the distal portion of the inner shaft. The distal nose may have a proximal end disposed distal to the implant holding region. The catheter apparatus may further comprise a stop block coupled to the distal portion of the inner shaft and disposed proximal to the implant holding region. The stop block may be fixedly coupled to the distal portion of the inner shaft.

The inner shaft of the catheter apparatus may comprise a hypotube having an inner lumen, and the inner lumen of the hypotube comprises a guidewire lumen.

The catheter apparatus may further comprise an anti-compression coil disposed between the inner shaft and the outer sheath to provide support for the inner shaft. The anti-compression coil may comprise a proximal end and a distal end. The proximal end of the anti-compression coil may be disposed distal to the at least one latch. The distal end of the anti-compression coil may be disposed proximal of the implant holding region of the inner shaft.

The outer sheath of the catheter apparatus nay have a larger diameter distal region configured to enclose the implant holding region and a smaller diameter proximal region. Proximal retraction of the larger diameter distal region may expose the implant holding region to allow the implant to be deployed. The catheter apparatus may further comprise a protective sleeve disposed over the smaller diameter proximal region. The protective sleeve may have a distal end, and a gap may be defined between the larger diameter distal region of the outer sheath and the distal end of the protective sleeve to allow the larger diameter distal region to be proximally retracted.

Aspects of the present disclosure provide methods of delivering one or more implants. In an exemplary method, a catheter apparatus may be advanced through a blood vessel to a target site. An outer sheath of the catheter apparatus may be retracted to expose the implant and allow the implant to be deployed. The implant may have been disposed on an implant holding region of an inner shaft of the catheter apparatus. A proximal end of the outer sheath may be coupled to at least one latch configured to resist retraction of the outer sheath. Retracting the outer sheath of the catheter apparatus may comprise tensioning at least one cable of the catheter apparatus over a threshold force, thereby releasing at least one latch to allow the at least one latch and the outer sheath to be proximally retracting. The implant may comprise a stent-graft, such as a femoral-popliteal stent-graft, and the implant may be is self-expanding. The blood vessel may comprise one or more of an aorta, a carotid artery, an external carotid artery, an internal carotid artery, a subclavian artery, an axillary artery, a brachial artery, a radial artery, an ulnar artery, a thoracic aorta, an abdominal aorta, a hypogastric artery, an external iliac artery, an internal iliac artery, a superior mesenteric artery, a renal artery, a femoral artery, a popliteal fossa, a popliteal artery, an anterior tibial artery, a dorsalis pedis artery, a posterior tibial artery, an arch of foot artery, a pulmonary vein, a vena cava, a superior vena cava, an inferior vena cava, a superior mesenteric vein, a jugular vein, an internal jugular vein, a subclavian vein, an axillary vein, a pulmonary artery, a cephalic vein, a basillic vein, a renal vein, a femoral vein, or a great saphenous vein.

The catheter apparatus may be advanced over a guidewire placed in the blood vessel. Tensioning the at least one cable may comprise actuating a pulley within a handle body of the catheter apparatus. The pulley may comprise a rotatable spool, and the pulley may be actuated by spinning the rotatable spool with a finger wheel on the handle body.

The at least one retractable latch may be biased to push outwardly into one or more slots in an inner track of a handle body of the catheter apparatus to resist proximal retraction. The tensioning of the at least one cable over the threshold force may cause the at least one retractable latch to retract from the one or more slots, thereby allowing proximal retraction of the outer sheath.

Alternatively or in combination, the at least one retractable latch may be biased to push outwardly against an inner track of a handle body of the catheter apparatus to provide friction to resist proximal retraction. The at least one latch may be released by changing a configuration of the at least one retractable latch to release from the inner track of the handle body.

Retracting the outer sheath of the catheter apparatus may comprise narrowing a gap between a larger diameter distal region of the outer sheath and a distal end of a protective sleeve disposed at least partially over a smaller diameter proximal region of the outer sheath. The larger diameter distal region may be configured to enclose the implant holding region of the inner shaft.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

The present disclosure provides systems, devices, and methods for delivering a medical implant, such as a bypass or stent graft, to a target site in a bodily vessel, such as a femoral artery or femoral vein. Exemplary catheter apparatuses for delivering the implant may comprise an inner shaft with an implant holding region and an outer sheath disposed at least over the implant holding region. The outer sheath may be proximally retracted to expose the implant at the implant holding region, allowing the implant to deploy such as by self-expansion. The catheter apparatus may be provided with a handle having latch mechanism(s) to control retraction. For instance, the latch mechanism(s) may allow the outer sheath to be retracted incrementally and may prevent the outer sheath from returning to a forward, implant constraining position. At least a portion of the outer sheath may be covered with a reinforcement sleeve. The reinforcement sleeve may isolate the outer sheath from fiction or impingement from an introducer sheath through which the catheter apparatus is advanced, the valve of such an introducer sheath, the physician's hand, the vessel wall, or other object or surfaces. The reinforcement sleeve or another structure such as a reinforcement coil may also provide column strength and/or torqueability to the catheter apparatus. The outer sheath may comprise a larger diameter distal region to constrain the implant and a smaller diameter proximal region, and a longitudinal gap may be defined between the proximal end of the larger diameter distal region of the outer sheath and a distal end of the reinforcement sleeve. The longitudinal gap may be reduced as the outer sheath is retracted.

Figure 1A:
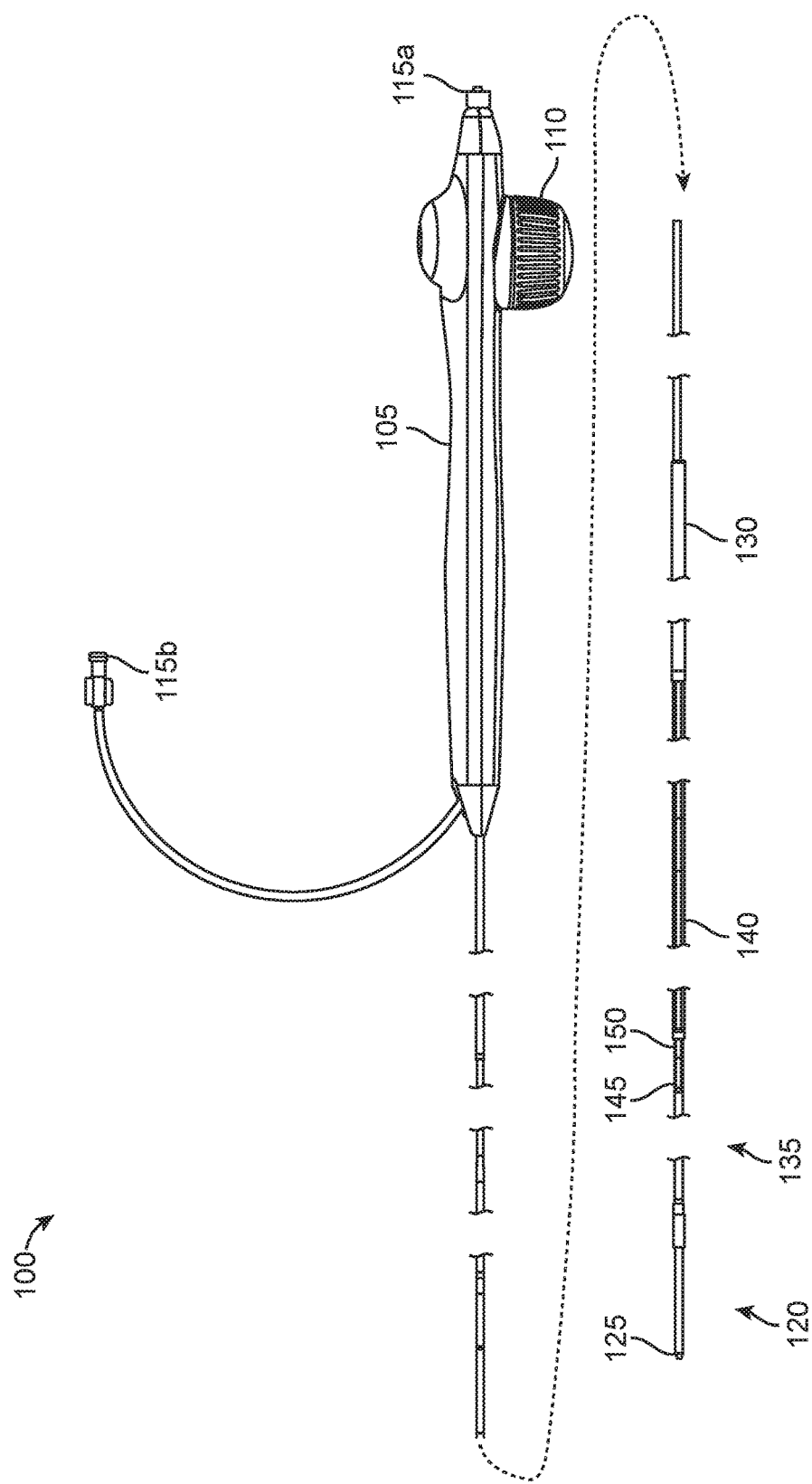
FIG. 1A shows a side view of a bypass or stent graft delivery apparatus, according to many embodiments.
Figure 1B:
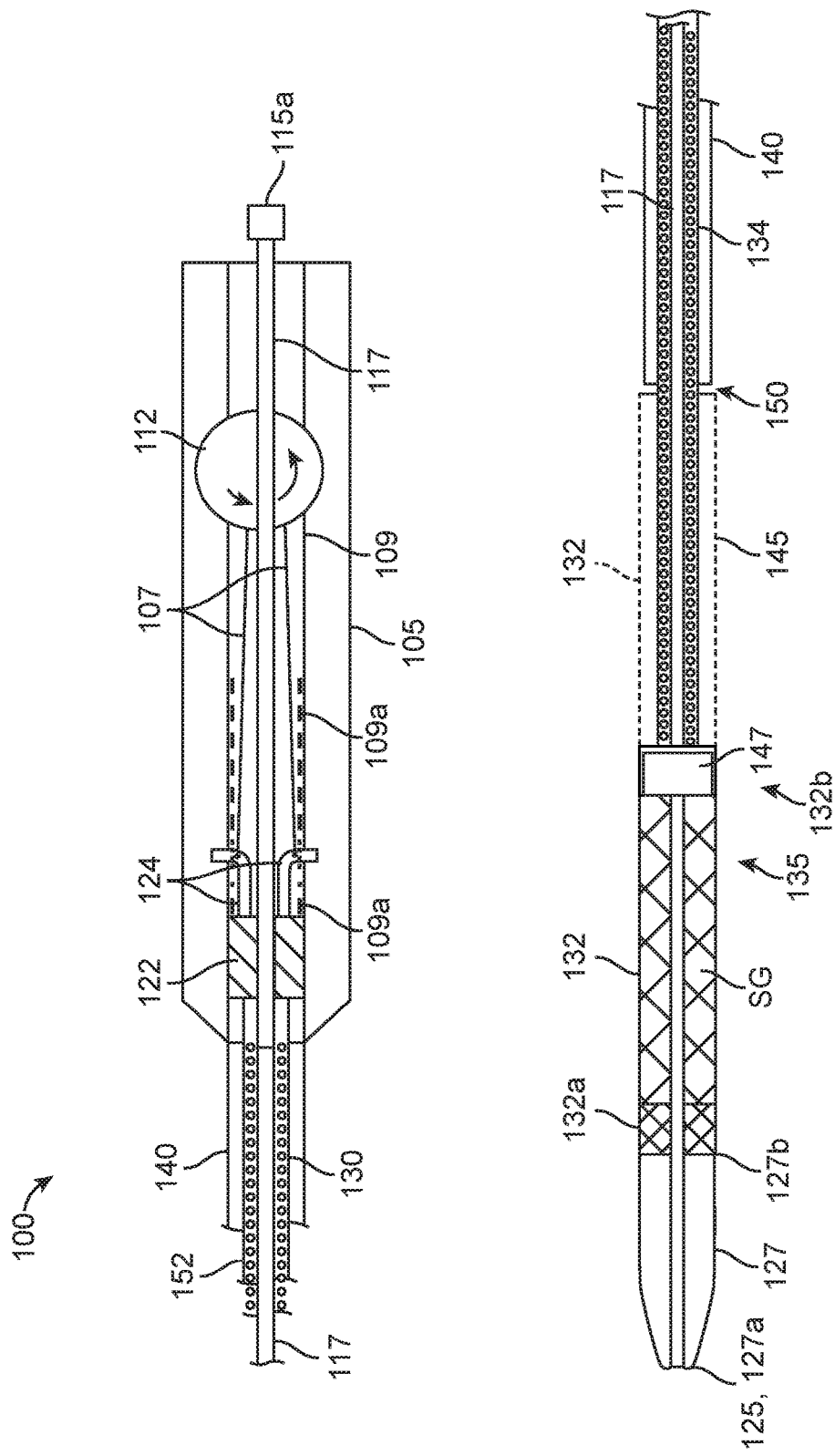
FIG. 1B shows a side sectional view of the bypass or stent graft delivery apparatus of FIG. 1A, showing in detail the proximal handle and the distal working end, according to many embodiments.

Referring now to FIGS. 1A-1E, an exemplary bypass or stent graft delivery catheter apparatus 100 is shown. FIG. 1A shows a side view of the catheter apparatus 100, and FIG. 1B shows a side, section view of the same. The catheter apparatus 100 will typically be advanced through an introducer sheath to reach a target location in a blood vessel(s). The introducer sheath may be a typical, commercially-available catheter introducer sheath such as a 5 Fr, 6 Fr, 7 Fr, 8 Fr, 9 Fr, 10 Fr, 11 Fr, or other size introducer sheath. The catheter apparatus 100 may be provided in one or more sizes to be compatible with a given size of introducer sheath.

The catheter apparatus 100 may comprise a proximal handle 105 and a working end 120, which may include a distal tip 125 and an outer sheath 130 disposed proximally of the distal tip 125. A knob 110 on the proximal handle 105 may be actuated to retract the outer sheath 130, exposing the stent graft holding region 135. The catheter apparatus 100 may further comprise a reinforcement sleeve 140 disposed over the outer sheath 130 proximally of the stent graft holding region 135. The reinforcement sleeve 140 may be fixed relative to the handle 105 while the outer sheath 130 may be retractable, and the reinforcement sleeve 140 may extend from the handle 105 to just proximal of the working end 120. A longitudinal gap 145 may be defined between an enlarged distal region 132 of the outer sheath 130 and a distal end or abutment 150 of the reinforcement sleeve 140 to accommodate the enlarged distal region 132 as the outer sheath 130 is retracted (see enlarged distal region 132 in the retracted configuration as shown by dotted line in FIG. 1B.) The enlarged distal region 132 will typically have the same outer diameter as the reinforcement sleeve 140 such that the at least the distal portion of the catheter apparatus 100 can have a smooth, consistently sized outer diameter such as to facilitate advancement. In some embodiments, the enlarged distal region 132 and the reinforcement sleeve 140 have different outer diameters. The proximal handle 105 may include one or more connectors or luer locks 115a, 115b to allow access to one or more internal lumens or tracks within the catheter apparatus 100.

As shown in FIG. 1B, the catheter apparatus 100 may further comprise a hypotube or inner shaft 117 which may be enclosed by the proximal handle 105 and the outer sheath 130. The hypotube or inner shaft 117 may be coaxial with the outer sheath 130. The inner shaft 117 may include an inner lumen such as a guidewire lumen that may be accessed through the connector or luer 115a. At the working end 120, the inner shaft 117 may be fixedly coupled to a distal nose 127, which may have a distal end 127a (which may also be the distal tip 125 of the catheter apparatus 100) and a proximal end 127b, and a stop block 147. The distal end 127a may be tapered to facilitate the advancement of catheter apparatus 100 through bodily vessels such as tortuous vasculature. The "landing zone" or stent graft holding region 135 may be defined between the proximal end 127b of the distal nose 127 and the stop block 147. The larger diameter or enlarged distal region 132 of the outer sheath 130 may constrain a bypass or stent graft SG at the stent graft holding region 135 as shown in FIG. 1B. Typically, the longitudinal gap 145 will be at least as long as the bypass or stent graft SG to provide enough space for the enlarged distal region 132 of the outer sheath 130 to be retracted so as to free the bypass or stent graft SG from constraint. In an example, the working length of the delivery catheter apparatus 100 (including the inner shaft 117 and the outer sheath 130) may be 135 cm, the stent graft holding region 135 may be slightly longer than the bypass or stent graft SG and have a diameter from 0.071" to 0.075", the inner diameter of the enlarged distal section 132 of the outer sheath 130 may be 0.098", the outer diameter of the of the enlarged distal section 132 of the outer sheath 130 may be 0.110", and the inner and outer diameters of the smaller diameter section of the outer sheath 130 may be 0.077" and 0.091", respectively.

To retract the outer sheath 130, the knob 110 at the proximal handle 105 may be actuated. As shown in FIGS. 1B and 1E, the knob 110 may be coupled to a rotating/ratcheting cable retraction spool 112 disposed within the proximal handle 105. Actuating or rotating the knob 110 may actuate the cable retraction spool 112. The outer sheath 130 may include a smaller diameter proximal region 134 and the outer sheath 130 may extend proximally to within the proximal handle 105. The cable retraction spool 112 may be operatively coupled to the outer sheath 130 through a sliding block 122 and one or more cables 107. Actuation of the cable retraction spool 112 may proximally retract the sliding block 112 within a sliding track 109 of the proximal handle, thereby retracting the outer sheath 130. The sliding block 112 may comprise one or more retractable latches 124 which may be coupled to the one or more cables 107 and may interface with the sliding track 109 to control proximal retraction. In some embodiments, the sliding track 109 may be slotted with a plurality of slots 109a and the retractable latch(es) 124 may be biased outward to clip onto one or more of the slots 109a. For example, the retractable latch(es) 124 may each comprise one or more detents to engage the slot(s) 109a to provide a mechanical slot. Upon tensioning of the cable(s) 107 with the cable retraction spool 112 and at a threshold amount of tension, the latch(es) 107 may deform (e.g., bend inward) and retract from its present slot 109a and allow for retraction of outer sheath 130. The latch(es) 107 may then clip onto another slot 109a to again prevent proximal retraction until the cable(s) 107 are tensioned at or beyond the threshold. Thus, both releasing the latch(es) 107 and retracting the outer sheath 130 may be accomplished in one single motion by rotating the cable retraction spool 112. Alternatively or in combination, the retractable latch(es) 124 may be biased outwardly to touchingly contact and frictionally interface with the sliding track 109, and the sliding block 122 and the outer sheath 130 may be immobilized from proximal retraction by friction. In some embodiments, the handle 105 may be provided with a further button to unlatch or otherwise disengage the latch(es) 107 and distally advance the sliding block 122 to allow the outer sheath 130 to be advanced distally.

As the outer sheath 130 is retracted, the enlarged distal region 132 covering the stent graft holding region 135 and the stent graft SG may be gradually retracted to expose the stent graft SG, which may increase a distance between a distal end 132a of the enlarged distal region 132 and the proximal end 127b of the distal nose 127. The stop block 147 may prevent proximal movement of the stent graft SG as the enlarged distal region 132 is proximally retracted. As shown in FIG. 1B, a longitudinal gap 145 may be defined between proximal end 132b of the enlarged distal region 132 and the distal end or abutment 150 of the reinforcement sleeve 140, and the gap 145 may be closed or reduced as the outer sheath 130 is proximally retracted.

The catheter apparatus 100 may further comprise an anti-compression coil 152 to provide column strength and/or torqueability. As shown in FIG. 1B, the anti-compression coil 152 may be co-axially disposed over the hypotube or inner shaft 117 and the proximal portion 134 of outer sheath 130. In the longitudinal direction, the anti-compression coil 152 may be disposed between the stop block 147 and the handle 105. At least the longitudinal ends of the anti-compression coil 152 may be fixedly coupled to the hypotube or inner shaft 117.

Figure 1C:
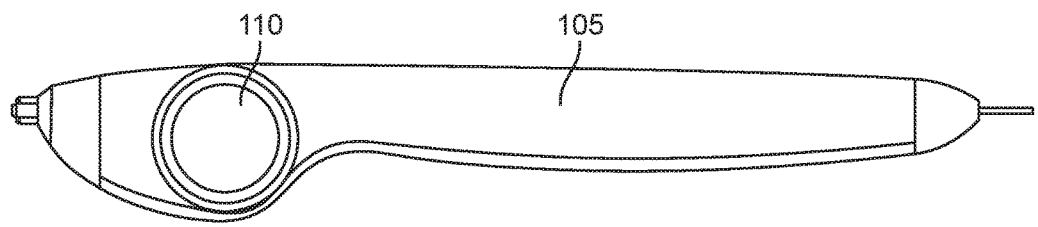
FIG. 1C shows a top view of the proximal handle of the bypass or stent graft delivery apparatus of FIG. 1A.
Figure 1D:
FIG. 1D shows a bottom view of the proximal handle of the bypass or stent graft delivery apparatus of FIG. 1A.
Figure 1E:
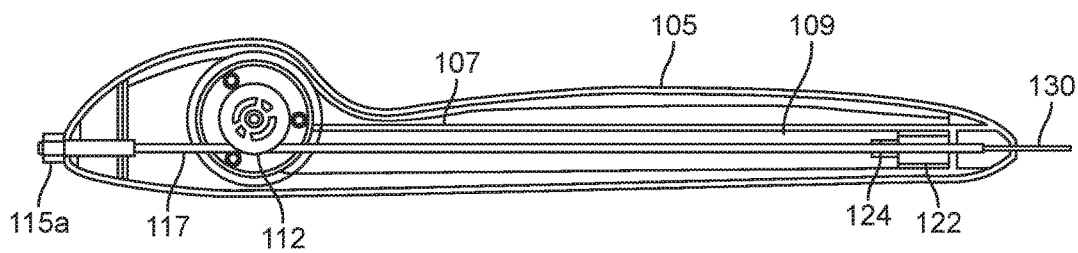
FIG. 1E shows a top, section view of the proximal handle of the bypass or stent graft delivery apparatus of FIG. 1A.

FIGS. 1C, 1D, and 1E respectively show a top view, a bottom view, and a bottom, sectional view of the proximal handle 105 of the bypass or stent graft delivery apparatus 100. The proximal handle 105 may be molded and ergonomically shaped to be hand-held. The knob 110 may comprise a finger or thumb wheel, which can be easily and intuitively actuated to deploy the stent graft SG as described herein.

Figure 2:
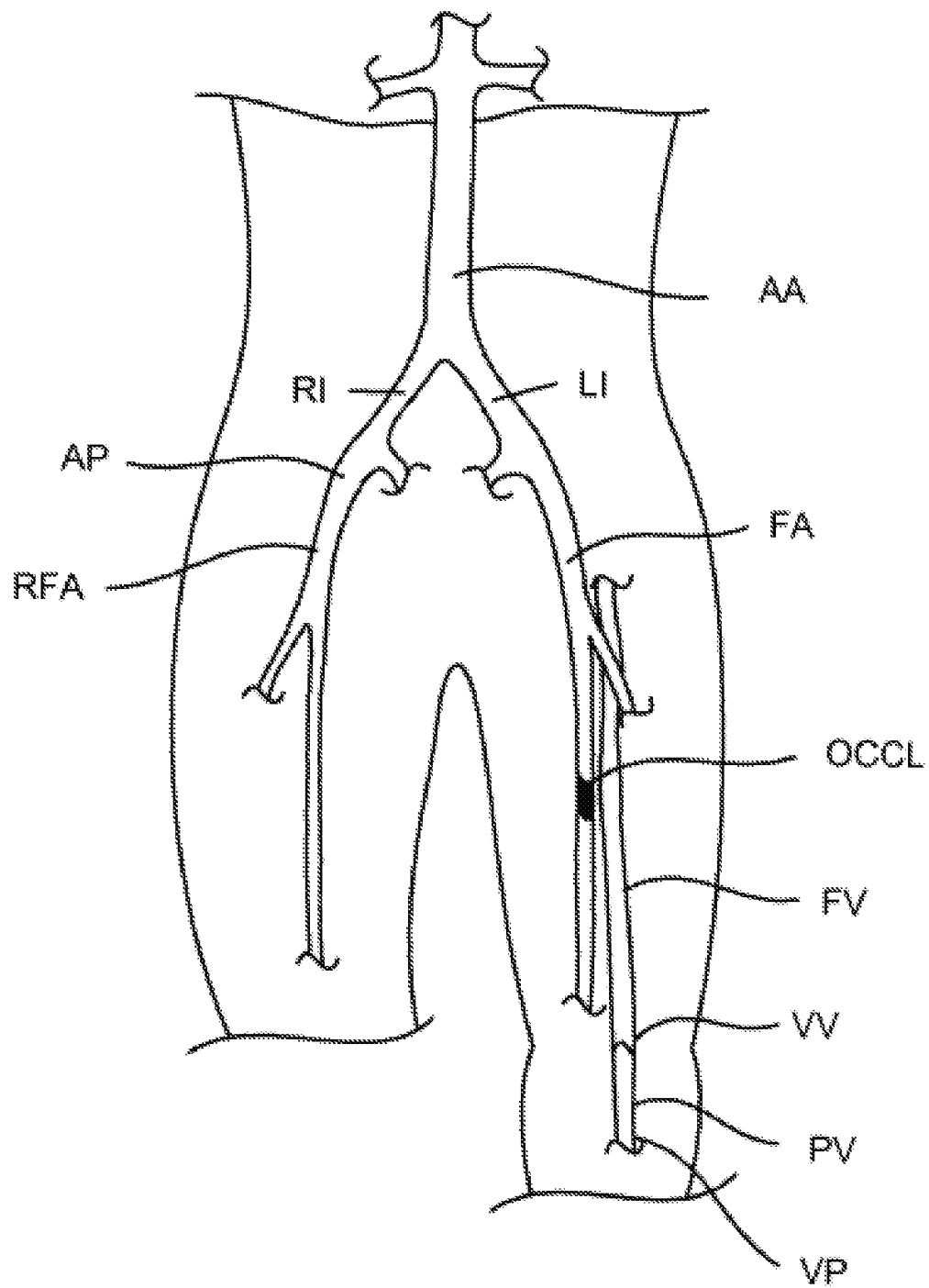
FIG. 2 illustrates the target anatomy to be treated by the methods and apparatus of the present disclosure including a femoral artery having an occlusion and an adjacent femoral vein which is used to bypass the occlusion. The view is anterior-posterior and would be reversed if taken from a supine point-of-view.

Referring to FIG. 2, the methods and systems of the present disclosure may be particularly suitable for implanting a bypass or stent graft to bypass an occlusion OCCL present in a femoral artery FA. As shown in FIG. 2, the occlusion OCCL is present in the right femoral artery, but the methods and systems would be suitable for treating occlusions in the left femoral artery, as well as all of the other peripheral arteries listed above. The anatomy includes a right femoral artery RFA and a left femoral artery FA, which both branch from the abdominal aorta AA through the right iliac artery RI and the left iliac artery LI. The methods of the present disclosure will typically be performed by introducing catheters from the "contralateral" artery into the "ipsilateral" artery over the branch between the iliacs.

The femoral artery FA runs parallel to the femoral vein FV. This is true, of course, in both legs although only the left femoral vein FV is shown in FIG. 2. The femoral vein FV extends downwardly and becomes the popliteal vein PV below the knee. Unlike the arteries, the femoral vein includes venous valves VV which inhibit retrograde flow of the venous blood away from the heart. The methods of the present disclosure may rely on advancing catheters though the popliteal vein PV and the femoral vein FV (and sometimes the tibial or other veins) only in an upward direction which minimizes any damage to the venous valves VV.

Referring now to FIGS. 3A-3M, methods for delivering bypass or stent grafts in accordance with the principles of the present disclosure will be described. The tools used in such methods may those as described in U.S. patent applications Ser. No. 13/868,804, filed Apr. 23, 2013 and now U.S. Pat. No. 9,259,340 issued on Feb. 16, 2016, and Ser. No. 15/001,086, filed Jan. 19, 2016, the full disclosures of which are incorporated herein by reference.

Figure 3A:
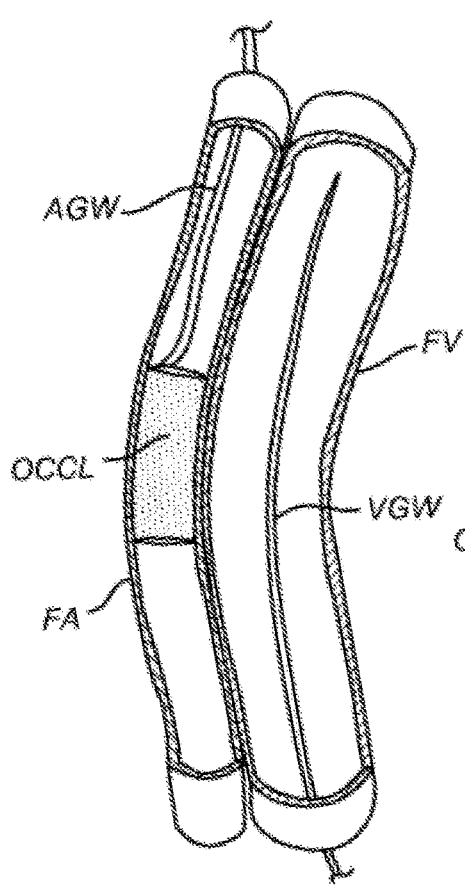
FIGS. 3A-3M illustrate methods of using a penetration catheter, a guidewire capture and stabilization catheter, and a stent graft delivery catheter for implanting a bypass or stent graft from the femoral artery into the femoral vein and back from the femoral vein into the femoral artery (or popliteal) to bypass the occlusion in the femoral artery, according to many embodiments.

As shown in FIG. 3A, an arterial access guidewire AGW may be introduced contralaterally from an access penetration AP, as shown in FIG. 2. The guidewire AGW may be advanced over the iliac artery bifurcation and down into the right femoral artery FA until it reaches the occlusion OCCL.

A venous guidewire VGW may be introduced upwardly in the femoral vein FV, typically from a location in the popliteal vein PV (FIG. 2) or a tibeal vein beneath the popliteal vein. The venous catheter will typically be introduced under fluoroscopic guidance. The arterial guidewire AGW will typically be introduced first, although the relative timing of introduction of the two guidewires is not critical.

Figure 3B:
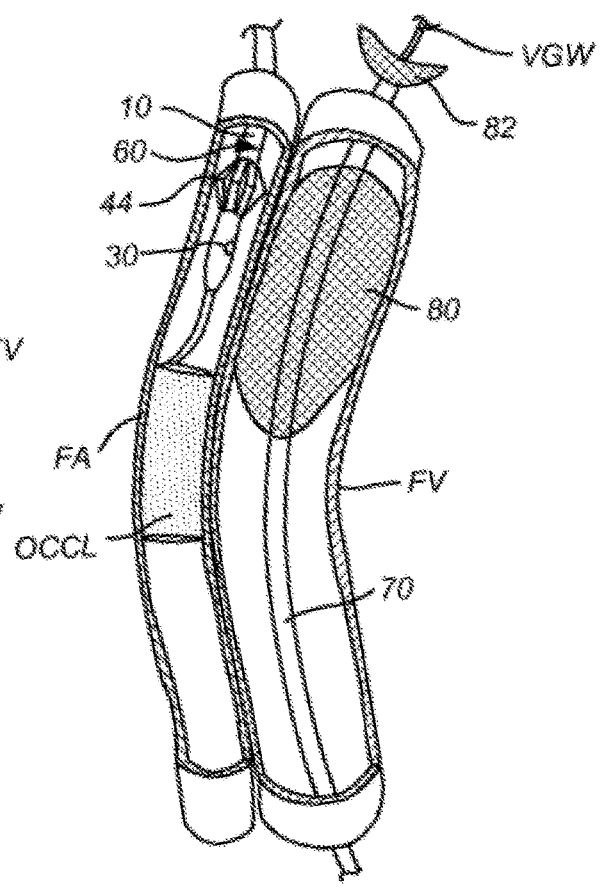

As shown in FIG. 3B, a penetration catheter 10 may be introduced over the arterial guidewire AGW and may be oriented using a rotational alignment marker 60 so that a penetration tool port 30 of the penetration catheter 10 may be aligned toward the femoral vein.

A guidewire capture and stabilization catheter 70 may be introduced upwardly in the femoral vein over the venous guidewire VGW so that a proximal expandable cage 80 of the guidewire capture and stabilization catheter 70 may be aligned at a position above the occlusion OCCL in the adjacent femoral artery FA. Usually, the guidewire capture and stabilization catheter 70 will be introduced before the penetration catheter 10 so that the expanded proximal cage 80 can act as a fluoroscopic marker in aligning the penetration tool port 30 under fluoroscopic imaging and can support the relatively flaccid vein to facilitate entry of the penetration tool.

As illustrated in FIG. 3B, the single expandable cage 44 may be expanded and located so that the penetration tool port 30 may be at a desired distance above the occlusion OCCL.

Figures 3C, 3D:
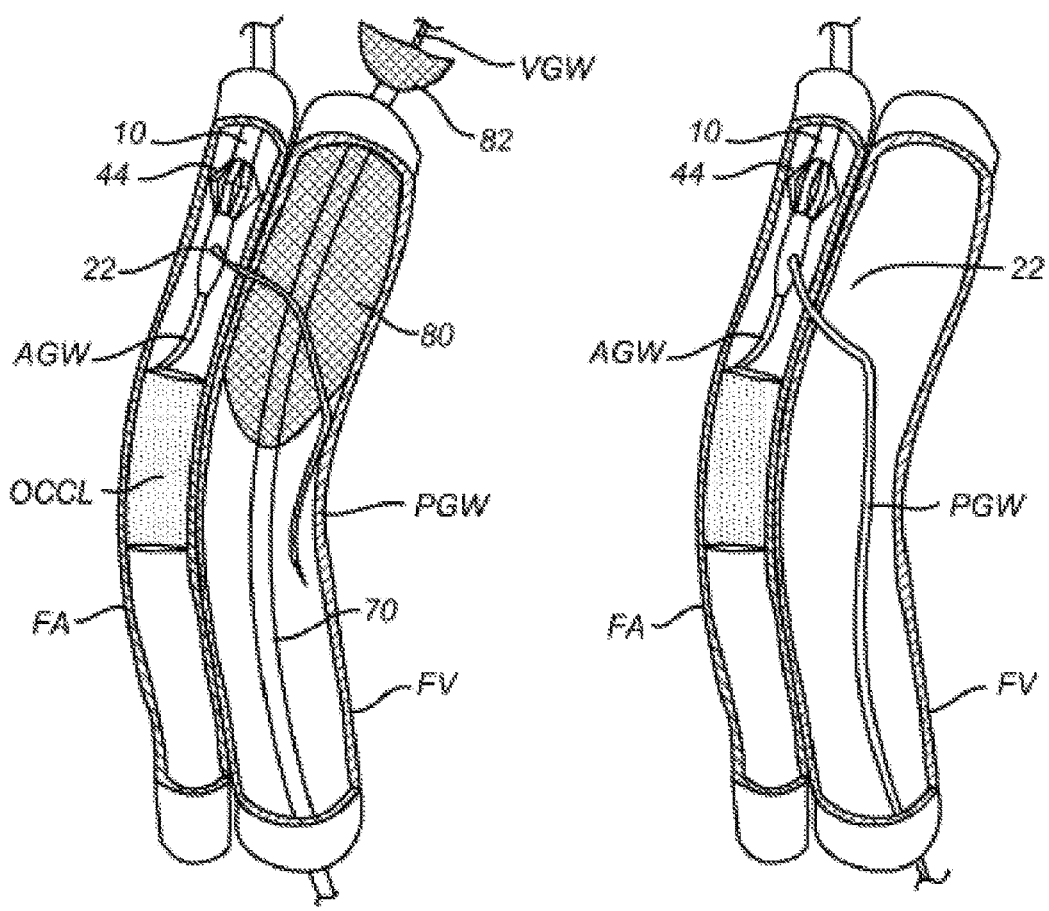
Figure 3E:
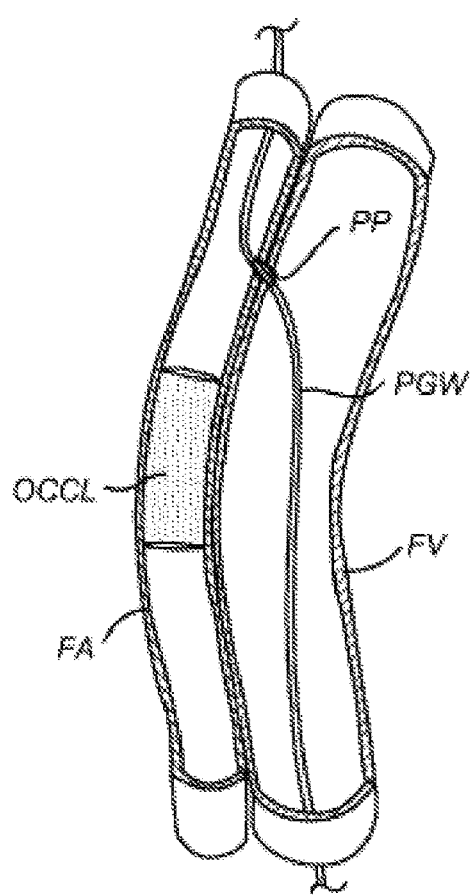

As shown in FIG. 3C, after the penetration catheter 10 and guidewire capture and stabilization catheter 70 are properly positioned and deployed, a penetration tool 22, typically a hollow needle having a sharpened distal tip but optionally any tubular or cannula member having a tissue-penetrating tip, such as an RF tip, at its distal end, may be advanced from the lumen of the femoral artery into the deployed proximal cage 80 within the lumen of the femoral vein FV. Once penetration of the penetrating tool 22 into the cage 80 is confirmed under fluoroscopic imaging, the penetrating guidewire PGW may be advanced from the tool 22 and downwardly out of the cage 80 into the lumen of the femoral vein FV. The penetration tool 22 may then be retracted into the penetration catheter 10, and the proximal cage 80 may be collapsed to capture the penetration guidewire PGW. After capturing the penetration guidewire PGW, the guidewire capture and stabilization catheter 70 may be withdrawn downwardly and removed from the lumen of the femoral vein FV so that the penetration guidewire PGW may be drawn outwardly through the left percutaneous penetration, typically from the popliteal vein PV (FIG. 2), as shown in FIG. 3D.

After the penetration guidewire PGW has been properly placed, the penetration catheter 10 may be removed, leaving the penetration guidewire extending from the contralateral introduction point AP (FIG. 2) to the venous penetration VP in the popliteal vein PV (FIG. 2). At this point, the proximal penetration PP (FIG. 3E) is typically dilated using a conventional balloon catheter. The catheter could be introduced through either penetration.

Figure 3F:
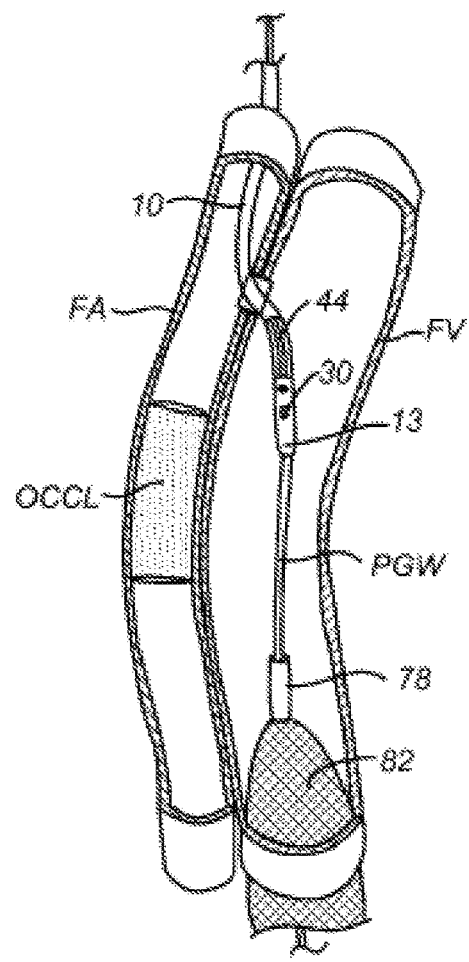

After the proximal penetration PP between the femoral artery FA and the femoral vein FV has been formed and dilated, the penetration catheter 10 may be reintroduced over the penetration guidewire PGW from the contralateral location, and the guidewire capture and stabilization catheter 70 may be reintroduced over the penetration guidewire PGW from the penetration VP in the popliteal or tibeal vein. The order of introduction is not critical and the two catheters may both be advanced into the lumen of the femoral vein, as shown in FIG. 3F. Typically, however, the capture and stabilization catheter 70 and the cages 80 and 82 may be deployed to stabilize and centrally align the penetration catheter 10 as it is introduced.

Figure 3G:
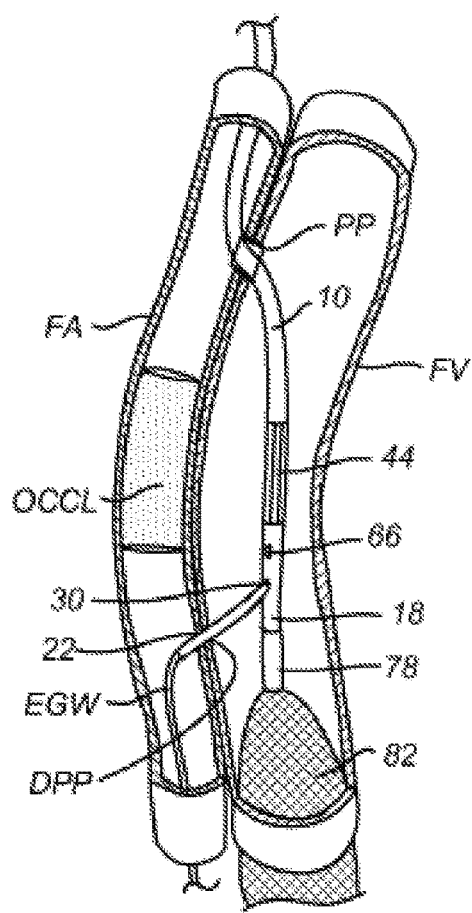

The distal end 18 of the penetration catheter 10 may be advanced so that it is received in the coupling receptacle 90 at the distal end 78 of the guidewire capture and stabilization catheter 70, as shown in FIG. 3G. Before completing such coupling, the distal end 18 of the penetration catheter may be rotationally aligned, using marker 66, so that the penetration tool port 30 may face the lumen of the femoral artery FA. Once the penetration port 30 is properly aligned, the penetration catheter 10 and the guidewire capture and stabilization catheter 70 may be coupled, and the distal cage 82 of the catheter 70 may be expanded to stabilize and center the distal end 18 of the penetration catheter 10. The penetration tool 22 may then be advanced into the lumen of the femoral artery 10 to form a distal penetration DPP, and an exchange guidewire EGW may be advanced through the lumen of the tool 22 into the lumen of the femoral artery below the occlusion.

It is of note that the stabilization element, cage 44, of the penetration tool does not have to be used during this portion of the procedure. In fact, a completely separate catheter could be used without having this stabilization feature included in the catheter. For convenience and reduction of cost, however, it may be desirable to re-use the same penetration catheter 10 which is used in forming the initial penetration PP on the proximal side of the occlusion OCCL.

Figure 3H:
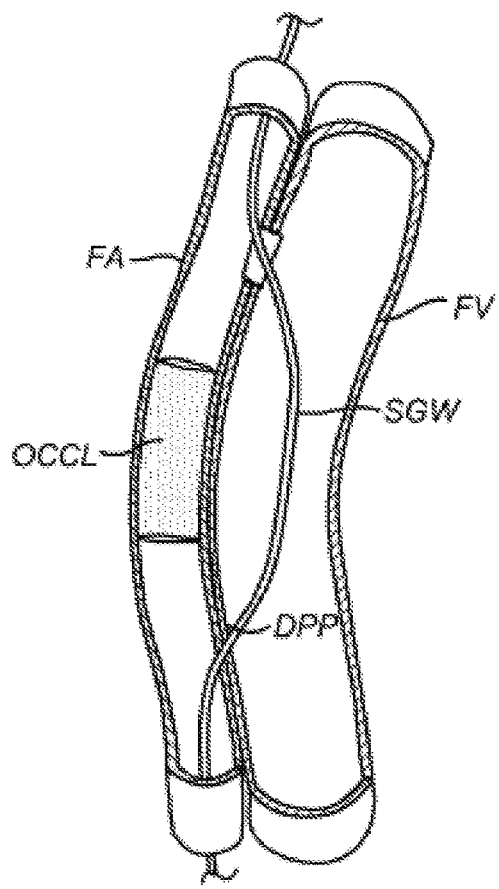

Once the exchange guidewire EGW is in place, each of the penetration catheter 10, the guidewire capture and stabilization catheter 70, and the penetration guidewire PGW may be removed from the patient, leaving only the exchange EGW in place, as shown in FIG. 3H, extending from the contralateral penetration into the femoral artery FA to a location well below the occlusion OCCL where it re-enters the arterial lumen. The exchange guidewire is typically a 0.014 in. wire and is typically exchanged for a 0.035 stent placement guidewire SGW. Once the stent placement guidewire SGW is in place, the distal penetration DPP will typically be dilated using a conventional balloon angioplasty catheter which is introduced contralaterally over the stent placement guidewire.

Figure 3I:
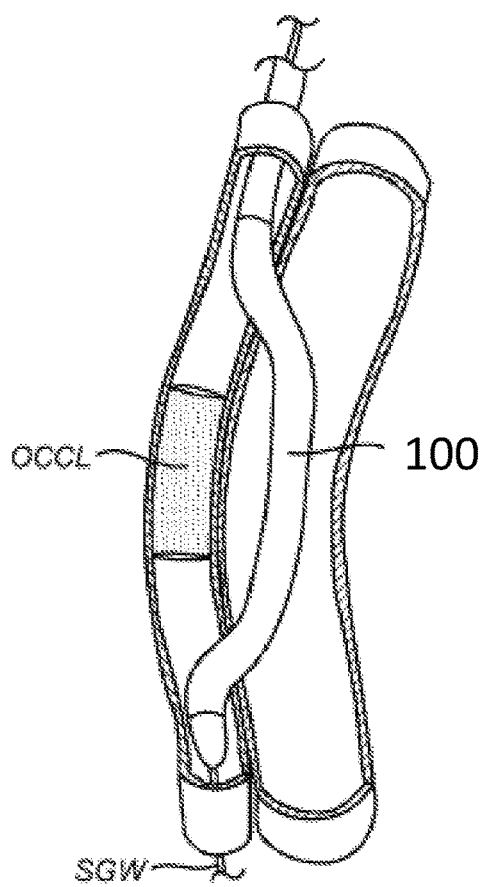
Figure 3J:
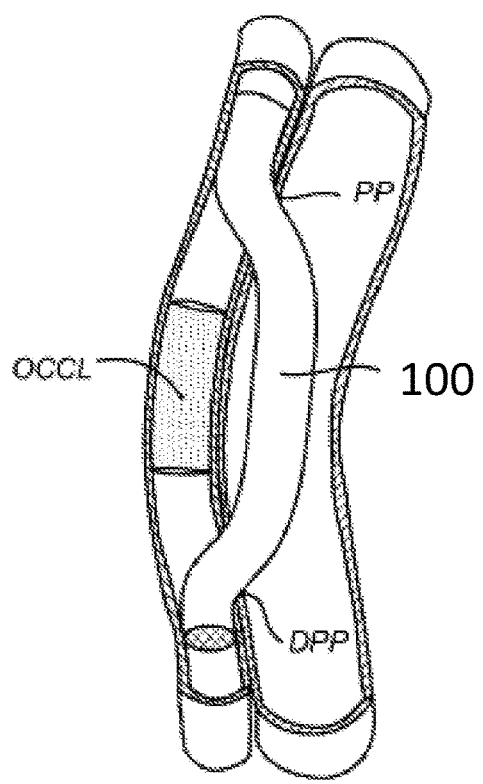
Figure 3K:
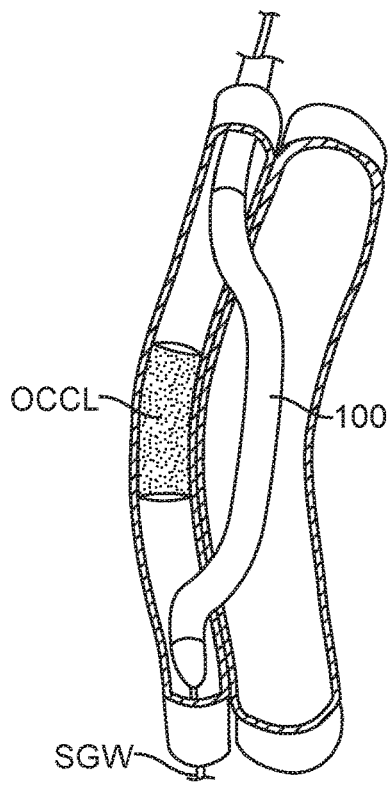
Figure 3L:
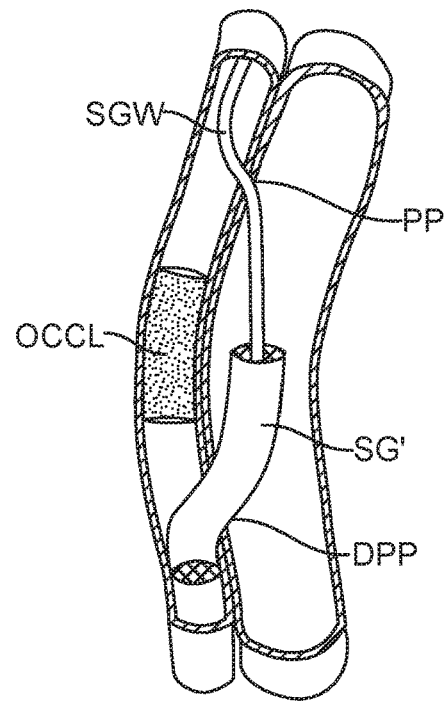
Figure 3M:
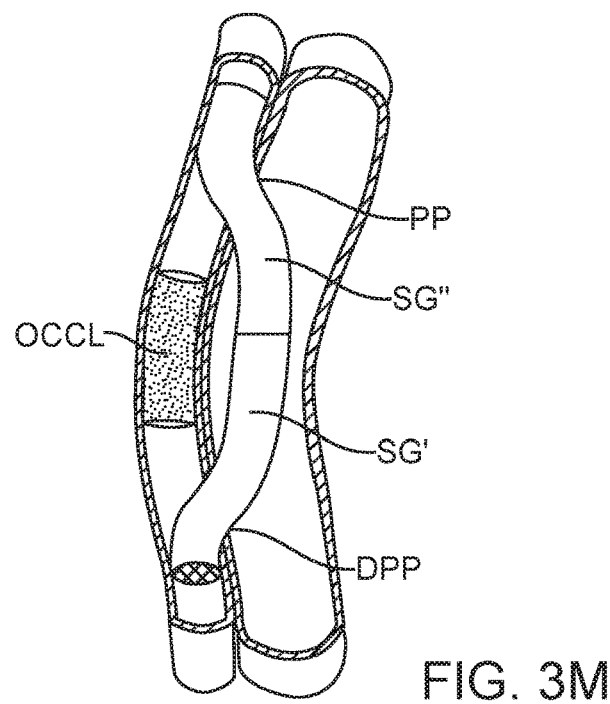

After dilation of the distal penetration DPP, the stent delivery catheter 100 may be introduced over the stent placement guidewire SGW from the contralateral penetration in the right femoral artery RFA (FIG. 2). The stent placement catheter 100 may carry the stent graft SG (or a plurality of stent grafts SG', SG"which can be formed in situ into an assembly of a desired length) capable of extending from the proximal penetration PP to the distal penetration DPP on either side of the occlusion OCCL, as shown in FIGS. 3I to 3J (showing the delivery of a single stent graft SG) and FIGS. 3K to 3M (showing the delivery of a first stent graft SG' (placed from the femoral vein FV to the femoral artery FA) and a second stent graft SG" (placed from the femoral artery FA to the femoral vein FV) which partially overlap and are formed in situ into a complete stent graft assembly). Suitable stent graft(s) SG will typically be self-expanding, comprising a self-expanding inner stent or scaffold covered by an outer graft structure. Suitable stent-grafts and delivery catheters are commercially available. An exemplary stent graft that may be introduced using the tools and methods of the present invention is described in commonly owned U.S. patent application Ser. No. 13/422,594 (published as US2012/0239137), the full disclosure of which is incorporated herein by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

What is claimed is:

1. A catheter apparatus for delivering an implant, the catheter apparatus comprising:
    an inner shaft having a proximal portion, a distal portion, and an implant holding region at the distal portion;
    an outer sheath disposed at least over the implant holding region of the inner shaft, the outer sheath being configured to be proximally retracted to expose an implant placed in the implant holding region to allow the implant to be deployed, and the retractable outer sheath having a proximal end and a distal end;
    at least one retractable latch coupled to the proximal end of the outer sheath and configured to resist retraction of the outer sheath;
    at least one cable coupled to the at least one retractable latch; and
    a handle body enclosing the proximal portion of the inner shaft and the proximal end of the outer shaft,
    wherein the latch mechanism is configured to be released upon tensioning of the at least one cable over a threshold force so that the proximal retraction of the at least one cable over the threshold force proximally retracts the at least one retractable latch and the outer sheath, and
    wherein the handle body comprises an inner track, wherein the at least one retractable latch is configured to releasably couple to the inner track of the handle body to resist proximal retraction, and wherein the tensioning of the at least one cable over the threshold force releases the at least one retractable latch from the inner track of the handle body.

2. The catheter apparatus of claim 1, wherein the at least one retractable latch is biased to push outwardly against the inner track of the handle body to provide friction to resist proximal retraction, and wherein the tensioning of the at least one cable over the threshold force changes a configuration of the at least one retractable latch to release from the inner track of the handle body.

3. The catheter apparatus of claim 1, wherein the inner track of the handle body comprises one or more slots, wherein the at least one retractable latch is biased to push outwardly into the one or more slots to resist proximal retraction, and wherein the tensioning of the at least one cable over the threshold force retracts the at least one retractable latch from the one or more slots thereby allowing proximal retraction of the outer sheath.

4. The catheter apparatus of claim 3, wherein the one or more slots comprises a plurality of slots.

5. The catheter apparatus of claim 1, further comprising a sliding block coupling the proximal end of the outer sheath to the at least one retractable latch, wherein the sliding block is configured to slide along the inner track of the handle body.

6. The catheter apparatus of claim 1, further comprising a pulley operatively coupled to the at least one cable, wherein the pulley is configured to be actuated to proximally retract the at least one cable, and wherein the pulley is housed at least partially within the handle body.

7. The catheter apparatus of claim 6, wherein the pulley comprises a rotatable spool.

8. The catheter apparatus of claim 7, further comprising a finger wheel coupled to handle body and the rotatable spool, wherein the finger wheel is configured to be spun to actuate the pulley.

9. The catheter apparatus of claim 1, wherein the at least one latch comprises a plurality of latches.

10. The catheter apparatus of claim 9, wherein the at least one cable comprises a plurality of cables, each cable of the plurality being coupled to a corresponding latch of the plurality of latches.

11. The catheter apparatus of claim 1, further comprising a distal nose coupled to the distal portion of the inner shaft, the distal nose having a proximal end disposed distal to the implant holding region.

12. The catheter apparatus of claim 1, further comprising a stop block coupled to the distal portion of the inner shaft and disposed proximal to the implant holding region.

13. The catheter apparatus of claim 12, wherein the stop block is fixedly coupled to the distal portion of the inner shaft.

14. The catheter apparatus of claim 1, wherein the inner shaft comprises a hypotube having an inner lumen.

15. The catheter apparatus of claim 14, wherein the inner lumen of the hypotube comprises a guidewire lumen.

16. The catheter apparatus of claim 1, further comprising an anti-compression coil disposed between the inner shaft and the outer sheath to provide support for the inner shaft.

17. The catheter apparatus of claim 16, wherein the anti-compression coil comprises a proximal end and a distal end.

18. The catheter apparatus of claim 17, wherein the proximal end of the anti-compression coil is disposed distal to the at least one latch.

19. The catheter apparatus of claim 17, wherein the distal end of the anti-compression coil is disposed proximal of the implant holding region of the inner shaft.

20. The catheter apparatus of claim 1, wherein the outer sheath has a larger diameter distal region configured to enclose the implant holding region and a smaller diameter proximal region, and wherein proximal retraction of the larger diameter distal region exposes the implant holding region to allow the implant to be deployed.

21. The catheter apparatus of claim 20, further comprising a protective sleeve disposed over the smaller diameter proximal region.

22. The catheter apparatus of claim 21, wherein the protective sleeve has a distal end, and wherein a gap is defined between the larger diameter distal region of the outer sheath and the distal end of the protective sleeve to allow the larger diameter distal region to be proximally retracted.

23. The catheter apparatus of claim 1, wherein the implant comprises a stent-graft.

24. The catheter apparatus of claim 1, wherein the implant is self-expanding.

25. A method of delivering an implant, the method comprising:
   advancing a catheter apparatus through a blood vessel to a target site; and
   retracting an outer sheath of the catheter apparatus to expose the implant and allow the implant to be deployed, the implant having been disposed on an implant holding region of an inner shaft of the catheter apparatus,
   wherein a proximal end of the outer sheath is coupled to at least one latch configured to resist retraction of the outer sheath,
   wherein retracting the outer sheath of the catheter apparatus comprises tensioning at least one cable of the catheter apparatus over a threshold force, thereby releasing at least one latch to allow the at least one latch and the outer sheath to be proximally retracted, and
   wherein the at least one retractable latch is biased to push outwardly against an inner track of a handle body of the catheter apparatus to provide friction to resist proximal retraction, and wherein the at least one latch is released by changing a configuration of the at least one retractable latch to release from the inner track of the handle body.

26. The method of claim 25, wherein the blood vessel comprises one or more of an aorta, a carotid artery, an external carotid artery, an internal carotid artery, a subclavian artery, an axillary artery, a brachial artery, a radial artery, an ulnar artery, a thoracic aorta, an abdominal aorta, a hypogastric artery, an external iliac artery, an internal iliac artery, a superior mesenteric artery, a renal artery, a femoral artery, a popliteal fossa, a popliteal artery, an anterior tibial artery, a dorsalis pedis artery, a posterior tibial artery, an arch of foot artery, a pulmonary vein, a vena cava, a superior vena cava, an inferior vena cava, a superior mesenteric vein, a jugular vein, an internal jugular vein, a subclavian vein, an axillary vein, a pulmonary artery, a cephalic vein, a basillic vein, a renal vein, a femoral vein, or a great saphenous vein.

27. The method of claim 25, wherein the catheter apparatus is advanced over a guidewire placed in the blood vessel.

28. The method of claim 25, wherein the implant comprises a stent-graft.

29. The method of claim 28, wherein the stent-graft comprises a femoral-popliteal stent-graft.

30. The method of claim 25, wherein the implant is self-expanding.

31. The method of claim 25, wherein tensioning the at least one cable comprises actuating a pulley within a handle body of the catheter apparatus.

32. The method of claim 31, wherein the pulley comprises a rotatable spool, and wherein actuating the pulley comprises spinning the rotatable spool with a finger wheel on the handle body.

33. The method of claim 25, wherein retracting the outer sheath of the catheter apparatus comprises narrowing a gap between a larger diameter distal region of the outer sheath and a distal end of a protective sleeve disposed at least partially over a smaller diameter proximal region of the outer sheath.

34. The method of claim 33, wherein the larger diameter distal region is configured to enclose the implant holding region of the inner shaft.

35. A method of delivering an implant, the method comprising:
   advancing a catheter apparatus through a blood vessel to a target site; and
   retracting an outer sheath of the catheter apparatus to expose the implant and allow the implant to be deployed, the implant having been disposed on an implant holding region of an inner shaft of the catheter apparatus,
   wherein a proximal end of the outer sheath is coupled to at least one latch configured to resist retraction of the outer sheath,
   wherein retracting the outer sheath of the catheter apparatus comprises tensioning at least one cable of the catheter apparatus over a threshold force, thereby releasing at least one latch to allow the at least one latch and the outer sheath to be proximally retracted, and
   wherein the at least one retractable latch is biased to push outwardly into one or more slots in an inner track of a handle body of the catheter apparatus to resist proximal retraction, and wherein the tensioning of the at least one cable over the threshold force retracts the at least one retractable latch from the one or more slots thereby allowing proximal retraction of the outer sheath.

36. The method of claim 35, wherein the blood vessel comprises one or more of an aorta, a carotid artery, an external carotid artery, an internal carotid artery, a subclavian artery, an axillary artery, a brachial artery, a radial artery, an ulnar artery, a thoracic aorta, an abdominal aorta, a hypogastric artery, an external iliac artery, an internal iliac artery, a superior mesenteric artery, a renal artery, a femoral artery, a popliteal fossa, a popliteal artery, an anterior tibial artery, a dorsalis pedis artery, a posterior tibial artery, an arch of foot artery, a pulmonary vein, a vena cava, a superior vena cava, an inferior vena cava, a superior mesenteric vein, a jugular vein, an internal jugular vein, a subclavian vein, an axillary vein, a pulmonary artery, a cephalic vein, a basillic vein, a renal vein, a femoral vein, or a great saphenous vein.

37. The method of claim 35, wherein the catheter apparatus is advanced over a guidewire placed in the blood vessel.

38. The method of claim 35, wherein the implant comprises a stent-graft.

39. The method of claim 38, wherein the stent-graft comprises a femoral-popliteal stent-graft.

40. The method of claim 35, wherein the implant is self-expanding.

41. The method of claim 35, wherein tensioning the at least one cable comprises actuating a pulley within a handle body of the catheter apparatus.

42. The method of claim 41, wherein the pulley comprises a rotatable spool, and wherein actuating the pulley comprises spinning the rotatable spool with a finger wheel on the handle body.

43. The method of claim 35, wherein the at least one retractable latch is biased to push outwardly against an inner track of a handle body of the catheter apparatus to provide friction to resist proximal retraction, and wherein the at least one latch is released by changing a configuration of the at least one retractable latch to release from the inner track of the handle body.

44. The method of claim 35, wherein retracting the outer sheath of the catheter apparatus comprises narrowing a gap between a larger diameter distal region of the outer sheath and a distal end of a protective sleeve disposed at least partially over a smaller diameter proximal region of the outer sheath.

45. The method of claim 44, wherein the larger diameter distal region is configured to enclose the implant holding region of the inner shaft.

\* \* \* \* \*